United States Patent
Zerkowski et al.

(10) Patent No.: US 11,234,818 B2
(45) Date of Patent: Feb. 1, 2022

(54) ANNULOPLASTY DEVICE

(71) Applicant: Medtentia International Ltd Oy, Espoo (FI)

(72) Inventors: Hans-Reinhard Zerkowski, Kreuzlingen (CH); Olli Keränen, Bjärred (SE); Johannes Jung, Pforzheim (DE)

(73) Assignee: Medtentia International Ltd Oy, Espoo (FI)

( * ) Notice: Subject to any disclaimer, the term of this patent is extended or adjusted under 35 U.S.C. 154(b) by 403 days.

(21) Appl. No.: 15/985,460

(22) Filed: May 21, 2018

(65) Prior Publication Data

US 2019/0350707 A1    Nov. 21, 2019

(51) Int. Cl.
*A61F 2/24* (2006.01)

(52) U.S. Cl.
CPC .......... *A61F 2/2445* (2013.01); *A61F 2/2409* (2013.01); *A61F 2230/0065* (2013.01); *A61F 2250/0018* (2013.01); *A61F 2250/0029* (2013.01)

(58) Field of Classification Search
CPC ........ A61F 2/24; A61F 2/2442; A61F 2/2445; A61F 2/2448; A61F 2/2451; A61F 2/2457; A61F 2/246; A61F 2/2469
See application file for complete search history.

(56) References Cited

U.S. PATENT DOCUMENTS

| | | | | |
|---|---|---|---|---|
| 6,964,684 | B2* | 11/2005 | Ortiz | A61F 2/2409 623/2.11 |
| 7,445,632 | B2* | 11/2008 | McGuckin, Jr. | A61F 2/2412 623/2.37 |
| 10,470,882 | B2* | 11/2019 | Gross | A61F 2/2445 |
| 10,722,359 | B2* | 7/2020 | Patel | A61F 2/2409 |
| 2012/0330411 | A1* | 12/2012 | Gross | A61F 2/2466 623/2.37 |
| 2018/0360605 | A1* | 12/2018 | Zerkowski | A61F 2/2466 |
| 2019/0000625 | A1* | 1/2019 | O'Carroll | A61F 2/2466 |
| 2019/0343631 | A1* | 11/2019 | McCarthy | A61F 2/2448 |
| 2020/0054453 | A1* | 2/2020 | Zerkowski | A61F 2/2448 |
| 2020/0093600 | A1* | 3/2020 | Keranen | A61B 17/072 |
| 2020/0107932 | A1* | 4/2020 | Rabito | A61F 2/246 |
| 2020/0107933 | A1* | 4/2020 | Oba | A61F 2/2442 |
| 2020/0138576 | A1* | 5/2020 | Tamir | A61F 2/2442 |
| 2020/0188110 | A1* | 6/2020 | Metcalf | A61F 2/2466 |
| 2020/0205974 | A1* | 7/2020 | Zerkowski | A61F 2/2463 |
| 2020/0205979 | A1* | 7/2020 | O'Carroll | A61F 2/2466 |
| 2020/0297491 | A1* | 9/2020 | Argento | A61F 2/2457 |
| 2021/0093452 | A1* | 4/2021 | Havel | A61F 2/2445 |
| 2021/0177597 | A1* | 6/2021 | Zerkowski | A61F 2/2445 |
| 2021/0212829 | A1* | 7/2021 | Keranen | A61F 2/2466 |

* cited by examiner

*Primary Examiner* — Seema Mathew
(74) *Attorney, Agent, or Firm* — Inskeep IP Group, Inc.

(57) ABSTRACT

An annuloplasty device is disclosed comprising first and second support rings being configured to be arranged as a coil in a first configuration around an axial direction, wherein the first and second support rings are configured to be arranged on opposite sides of native heart valve leaflets of a heart valve, a stiffening unit, wherein at least part of the first and second support rings comprises an interior channel configured to receive the stiffening unit, wherein insertion of the stiffening unit into the interior channel increases the stiffness of the first and/or second support rings. A method of repairing a defective heart valve is also disclosed.

9 Claims, 15 Drawing Sheets

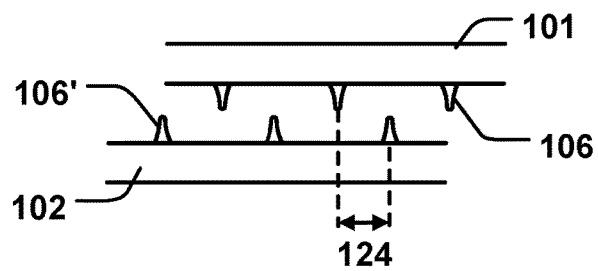
Fig. 7e
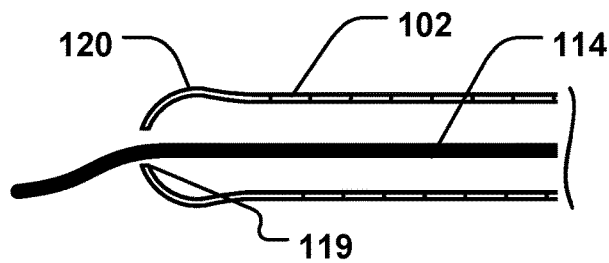 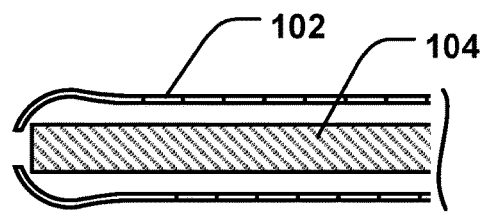
Fig. 7f          Fig. 7g
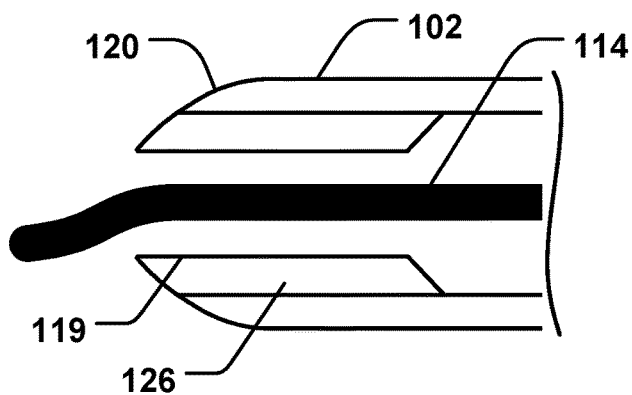 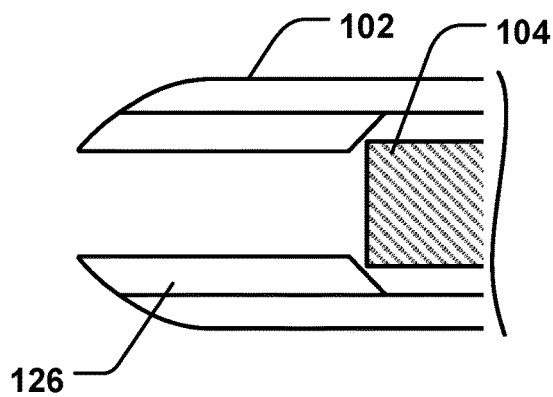
Fig. 7h          Fig. 7i

ANNULOPLASTY DEVICE

FIELD OF THE INVENTION

This invention pertains in general to the field of cardiac valve repair. More particularly the invention relates to an annuloplasty device, such as an annuloplasty ring or helix, for positioning at the heart valve annulus and a method of repairing a defective heart valve.

BACKGROUND OF THE INVENTION

Diseased mitral and tricuspid valves frequently need replacement or repair. The mitral and tricuspid valve leaflets or supporting chordae may degenerate and weaken or the annulus may dilate leading to valve leak. Mitral and tricuspid valve replacement and repair are frequently performed with aid of an annuloplasty ring, used to reduce the diameter of the annulus, or modify the geometry of the annulus in any other way, or aid as a generally supporting structure during the valve replacement or repair procedure. The annuloplasty ring is typically implanted around the annulus of the heart valve.

A problem with prior art annuloplasty implants is to achieve correct positioning at the heart valve and fixate the implant in the correct position. Suturing devices for annuloplasty implants have disadvantages that makes it difficult to suture in the correct position, thereby resulting insufficient suturing strength, and also in a very time-consuming procedure, which increases the risks for the patient. Furthermore, suturing devices are often not sufficiently compact for catheter based procedures. The use of clips for positioning annuloplasty implants is also associated with challenges, in particular when implanting helix rings that are to be positioned on either side of a heart valve. Insufficient fixation of such implant lead to traumatic effects since the fixation structure must ensure the correct position of the device over time. A further problem in the prior art is thus also to achieve a reliable fixation at the annulus of the heart valve. An annuloplasty implant is intended to function for years and years, so it is critical with long term stability in this regard.

The above problems may have dire consequences for the patient and the health care system. Patient risk is increased.

Hence, an improved annuloplasty device would be advantageous and in particular allowing for avoiding more of the above mentioned problems and compromises, and in particular ensuring secure fixation of the annuloplasty device, during the implantation phase, and for long-term functioning, in addition to a less complex procedure, and increased patient safety. A related method would also be advantageous.

SUMMARY OF THE INVENTION

Accordingly, examples of the present invention preferably seek to mitigate, alleviate or eliminate one or more deficiencies, disadvantages or issues in the art, such as the above-identified, singly or in any combination by providing a device according to the appended patent claims.

According to a first aspect an annuloplasty device is provided comprising first and second support rings being configured to be arranged as a coil in a first configuration around an axial direction, wherein the first and second support rings are configured to be arranged on opposite sides of native heart valve leaflets of a heart valve, a stiffening unit, wherein at least part of the first and second support rings comprises an interior channel configured to receive the stiffening unit, wherein insertion of the stiffening unit into the interior channel increases the stiffness of the first and/or second support rings.

According to a second aspect a method of repairing a defective heart valve is provided comprising positioning first and second support rings of an annuloplasty device in a first configuration as a coil on opposite sides of native heart valve leaflets of the heart valve, and increasing the stiffness of the first and/or second support rings by inserting a stiffening unit into an interior channel arranged in at least part of the first and/or second support rings.

Further examples of the invention are defined in the dependent claims, wherein features for the second aspect are as for the first aspect mutatis mutandis.

Some examples of the disclosure provide for a facilitated positioning of an annuloplasty device at a heart valve.

Some examples of the disclosure provide for a facilitated fixation of an annuloplasty device at a heart valve.

Some examples of the disclosure provide for a less time-consuming fixation of an annuloplasty to a target site.

Some examples of the disclosure provide for securing long-term functioning and position of an annuloplasty device.

Some examples of the disclosure provide for a reduced risk of damaging the anatomy of the heart such as the annulus or the valve leaflets.

Some examples of the disclosure provide for facilitated guidance of an annuloplasty device to an annulus of a heart valve.

Some examples of the disclosure provide for a more secure implantation of an annuloplasty device in narrow anatomies.

Some examples of the disclosure provide for avoiding interference of the annuloplasty device with the chordae of the valve leaflets.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIGS. 7b-c and 7f-i are schematic illustrations, in side view sections, of a distal portion of a support ring of an annuloplasty device, according to an example;

FIG. 7e is a schematic detail in a side view of an annuloplasty device, according to an example;

DESCRIPTION OF EMBODIMENTS

Figure 1A:
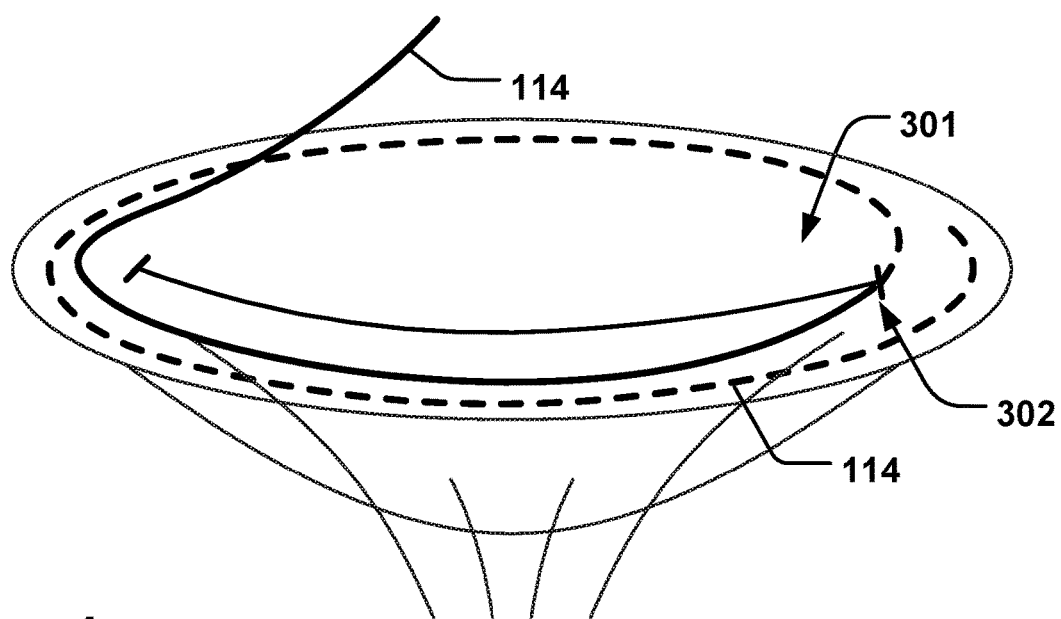
FIGS. 1a and 1c are schematic illustrations of a guide wire (end section thereof in FIG. 1b) arranged at opposite sides of the leaflets of a heart valve.
Figure 1B:
Figure 1C:
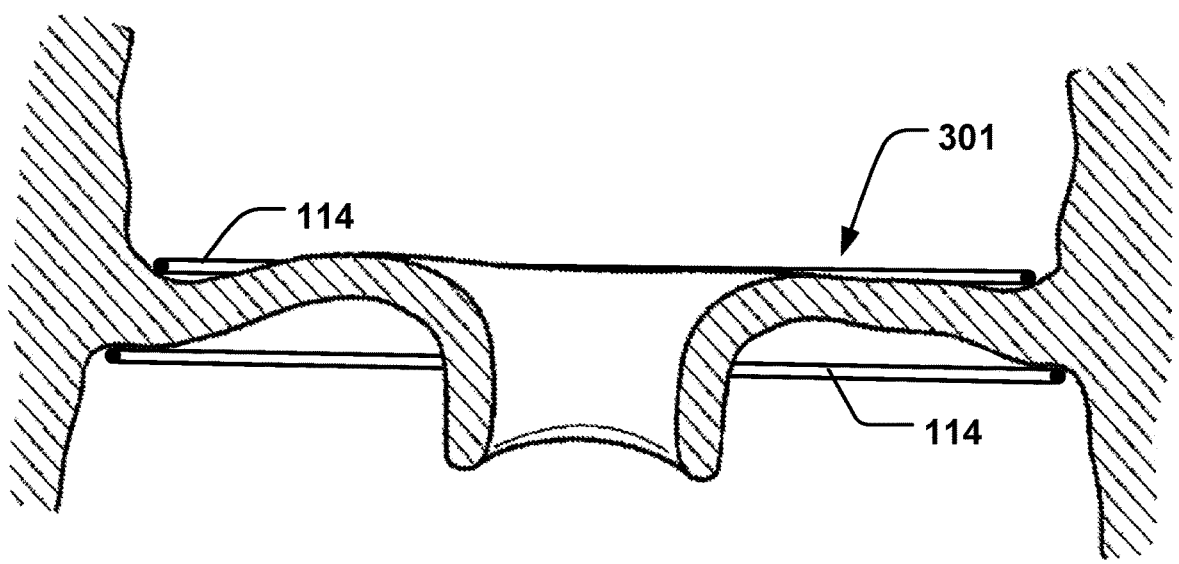

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to cardiac valve implants such as annuloplasty rings. However, it will be appreciated that the invention is not limited to this application but may be applied to many other annuloplasty implants and cardiac valve implants including for example replacement valves, and other medical implantable devices.

Figure 3A:
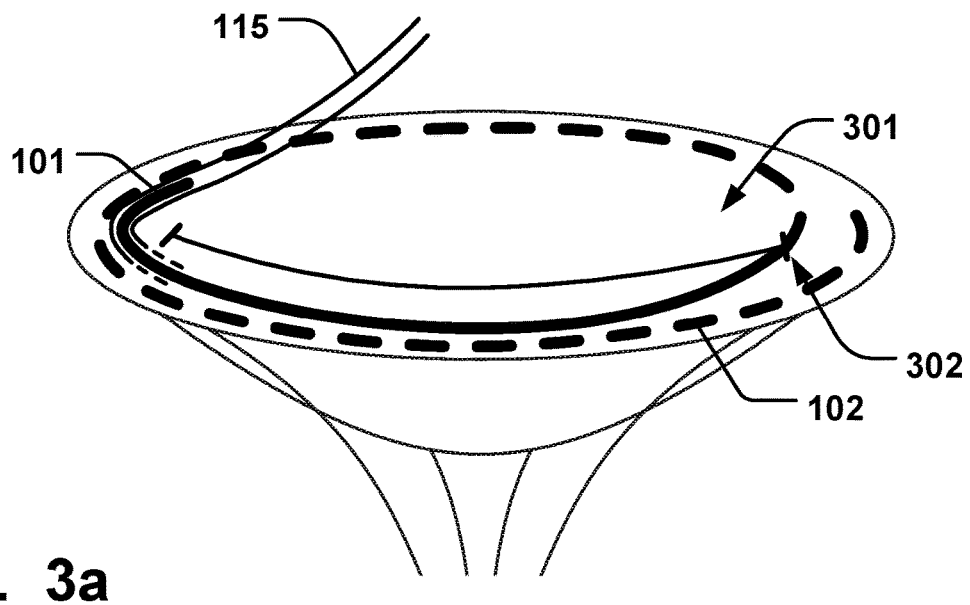
FIGS. 3a and 3d are schematic illustrations of first and second support rings of an annuloplasty device and a surrounding sheath arranged in a coiled configuration on opposite sides of heart valve leaflets, according to an example.
Figure 3B:
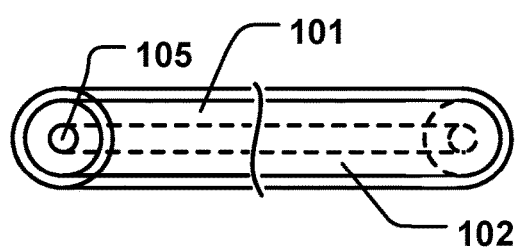
FIGS. 3b and 3c are schematic illustrations, in cross-sectional views, of support rings of an annuloplasty device arranged in a surrounding sheath.
Figure 3C:
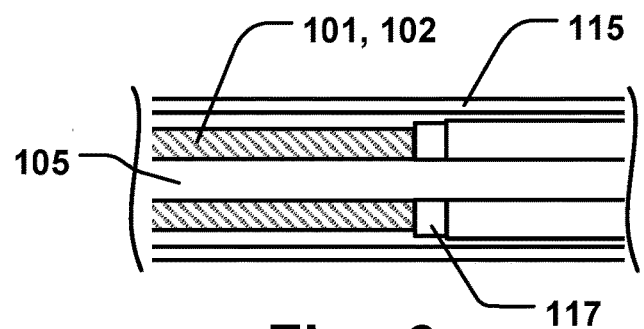
Figure 3D:
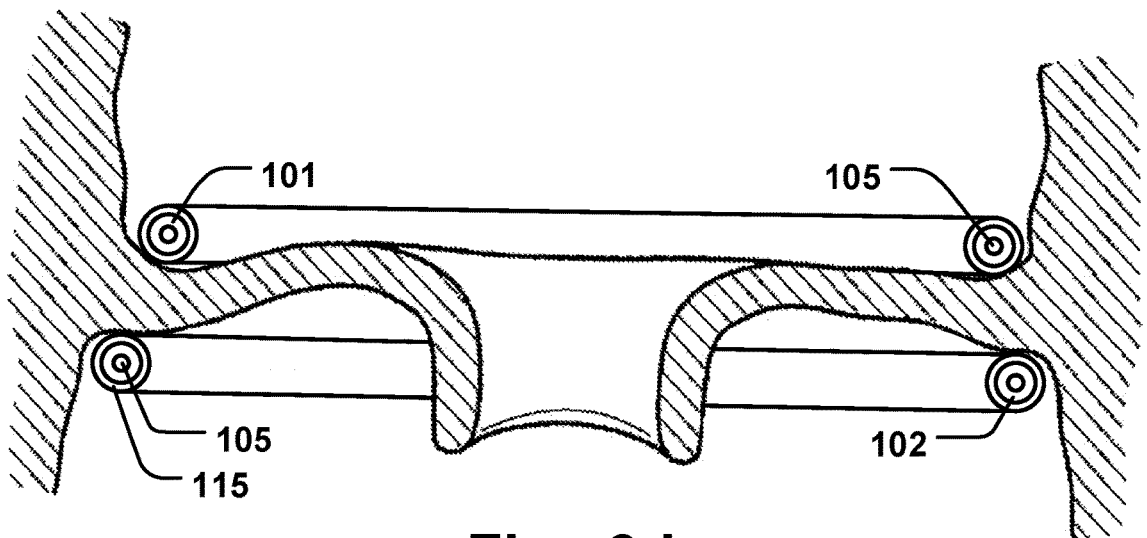
Figure 4A:
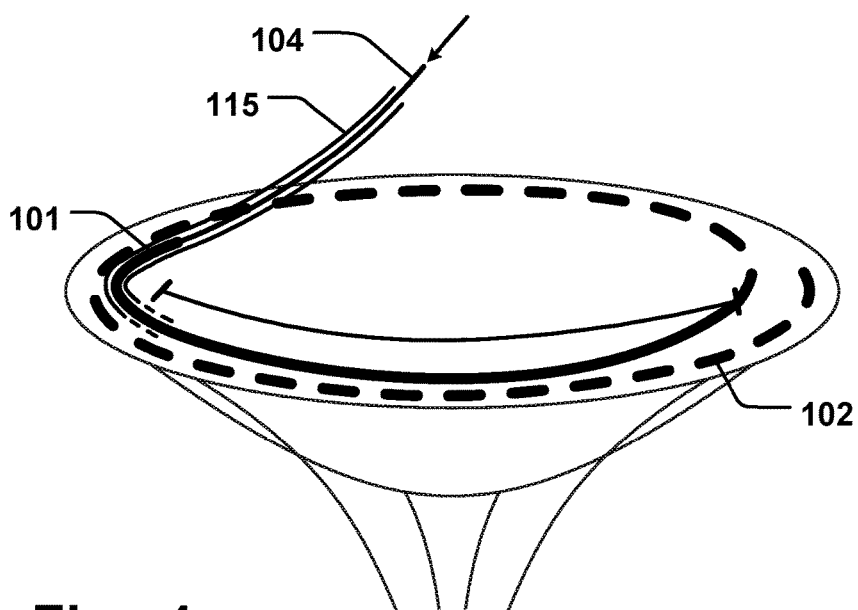
FIGS. 4a and 4d are schematic illustrations of a stiffening unit inserted into an interior channel of first and second support rings when arranged in a coiled configuration on opposite sides of heart valve leaflets, and a surrounding sheath, according to an example.
Figure 4B:
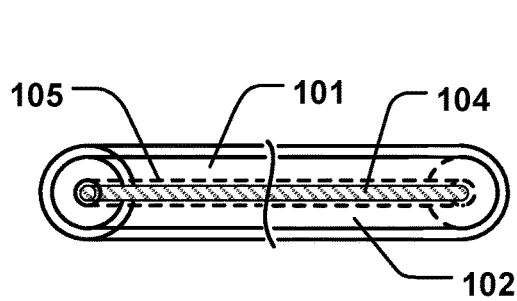
FIGS. 4b and 4c are schematic illustrations, in cross-sectional views, of a stiffening unit inserted into an interior channel of first and second support rings, according to an example.
Figure 4C:
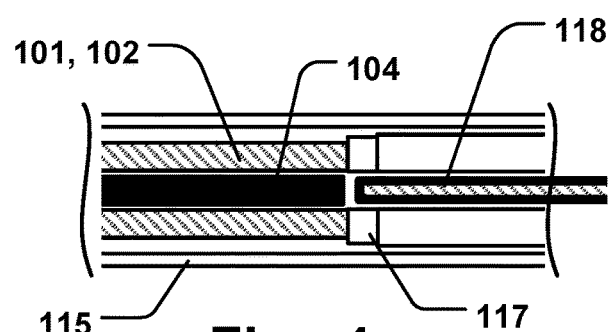
Figure 4D:
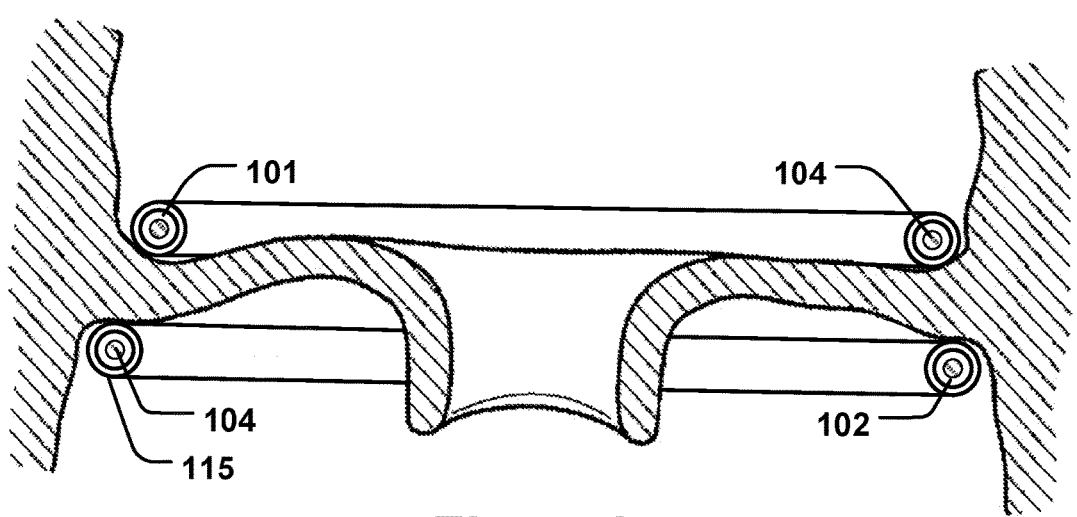
Figure 5A:
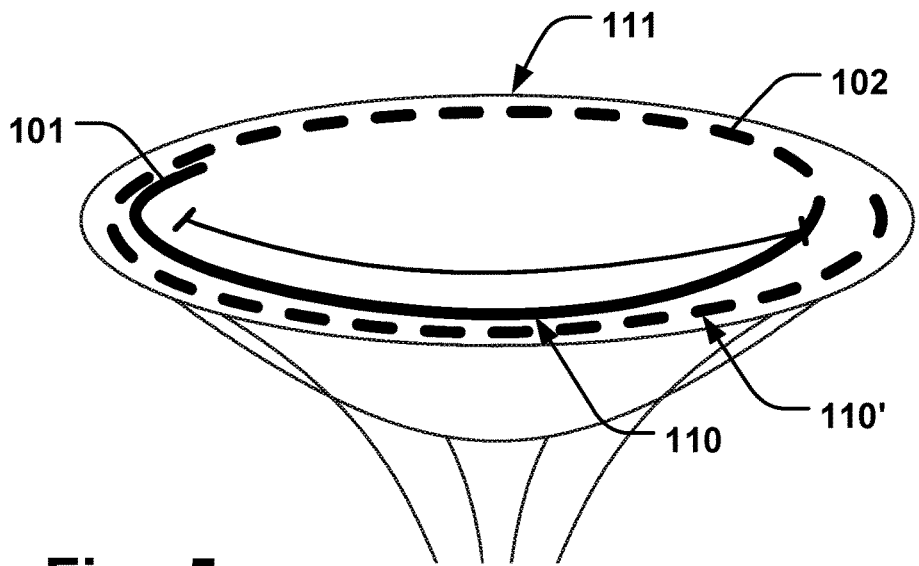
FIGS. 5a and 5d are schematic illustrations of first and second support rings, with an interior stiffening unit, arranged in a coiled configuration on opposite sides of heart valve leaflets, when the sheath is retracted, according to an example.
Figure 5B:
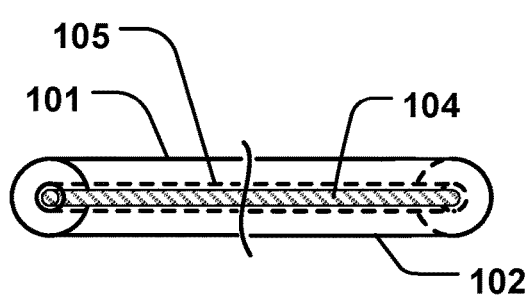
FIGS. 5b and 5c are schematic illustrations, in cross-sectional views, of a stiffening unit inserted into an interior channel of first and second support rings, according to an example.
Figure 5C:
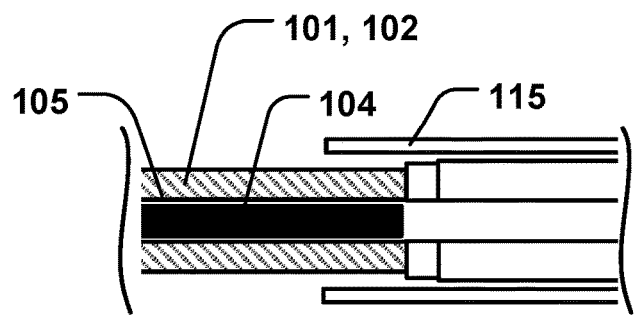
Figure 5D:
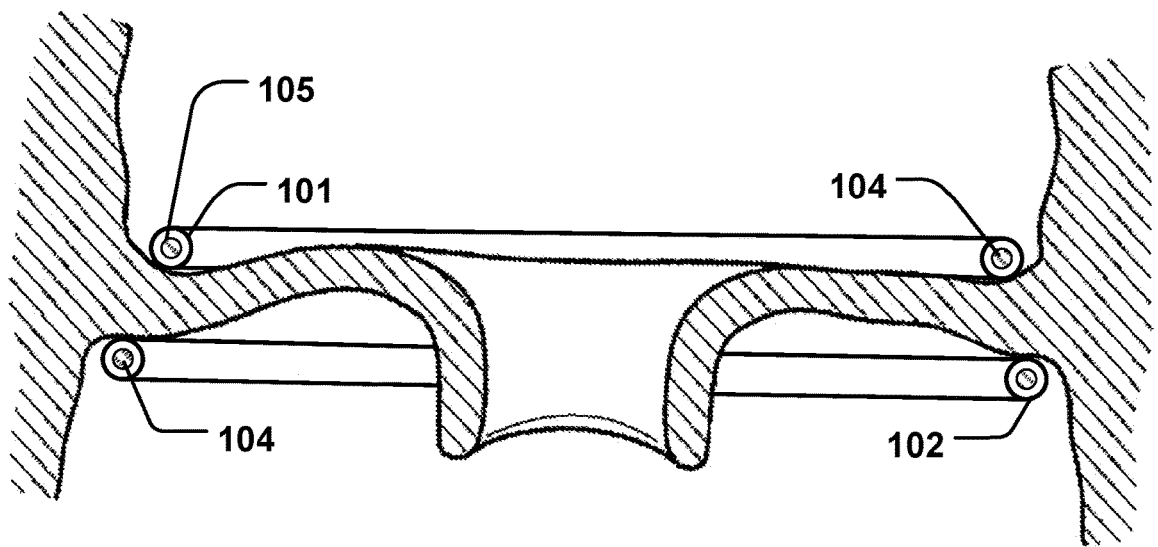
Figure 9A:
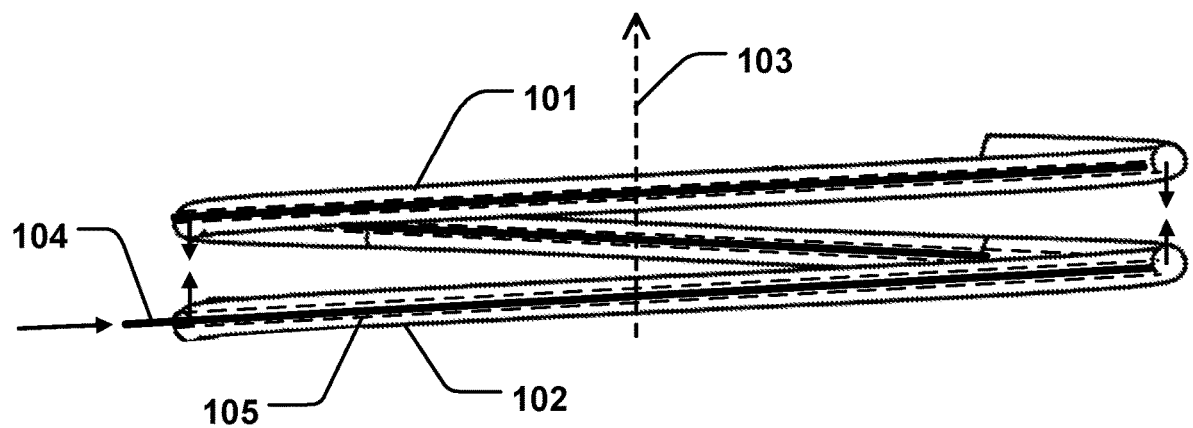
FIG. 9a is a schematic illustration of an annuloplasty device comprising an interior channel, in a side view, and a stiffening unit arranged in the interior channel, according to an example.

FIG. 9a is a schematic illustration of an annuloplasty device 100 comprising first 101 and second 102 support rings being configured to be arranged as a coil in a first configuration around an axial direction 103. The first and second support rings 101, 102, are configured to be arranged on opposite sides of native heart valve leaflets 301 of a heart valve, as illustrated in e.g. FIGS. 3a and 3d. As shown in FIG. 3d, the first support ring 101 may be arranged on an atrial side of the heart valve, and the second support ring 102 may be arranged on a ventricular side (also shown with dashed lines in FIG. 3a). The first support ring 101 thus extends along the annulus of the heart valve. The first and second support rings 101, 102, are connected to form a coil- or helix shaped ring. The coil extends through the valve opening at a commissure 302 thereof, as schematically illustrated in e.g. FIG. 3a. The annuloplasty device 100 further comprises a stiffening unit 104, where at least part of the first and second support rings 101, 102, comprises an interior channel 105 configured to receive the stiffening unit 104. FIGS. 5b, 5c, and 5d, show an example where a stiffening unit 104 is arranged in an interior channel 105 of the annuloplasty device 100. In this example, the interior channel 105 extends through both the first and second support rings 101, 102, and the stiffening unit 104 may thus extend through both said rings 101, 102. The stiffening unit 104 may thus be arranged as an interior coil inside the interior channel 105. It is conceivable however that the interior channel 105 and the stiffening unit 104 may extend through only one of the first and second support rings 101, 102. FIGS. 3b-d show the support rings 101, 102, with the interior channel 105 before the stiffening unit 104 has been positioned therethrough. FIG. 3c show a schematic delivery device 117 connected to a proximal end of the annuloplasty device 100, which may be a proximal end of the first support ring 101. The stiffening unit 104 may be positioned in the interior channel 105 via insertion through the delivery device 117, as schematically shown in FIG. 4c. In one example, an additional delivery unit 118, as shown in FIG. 4c, may be configured to deliver the stiffening unit 104 to the interior channel 105. The stiffening unit 104 increases the stiffness of the first and/or second support rings 101, 102. The rigidity of the first and/or second support rings 101, 102, is thus increased. I.e. the extent to which the rings 101, 102, resists deformation in response to an applied force is increased. In the examples shown in e.g. FIG. 5d, the stiffening unit 104 is arranged through both rings 101, 102. Thus, the stiffness of the rings 101, 102, is increased. The force by which the support rings 101, 102, pinch the leaflets from the opposite sides thereof may thus be increased, since the flexibility is reduced. This provides for facilitating a secure positioning of the first and second support rings 101, 102, at the opposite sides of the heart valve. At the same time, the support rings 101, 102, may be readily positioned at the correct position at the opposite sides of the heart valve before the stiffening unit 104 is arranged in the interior channel 105. Thus, having the stiffening unit 104 arranged in the first and second support rings 101, 102, provides for minimizing the risk of dislocation from the annulus, while providing for an easier implantation procedure. The procedure may thus be performed in a shorter amount of time. This also provides for enhancing cell growth in the vicinity of the support rings 101, 102, and a quicker healing. The device 100 as described thus also improves the long-term outcome of the valve repair procedure.

Figure 4E:
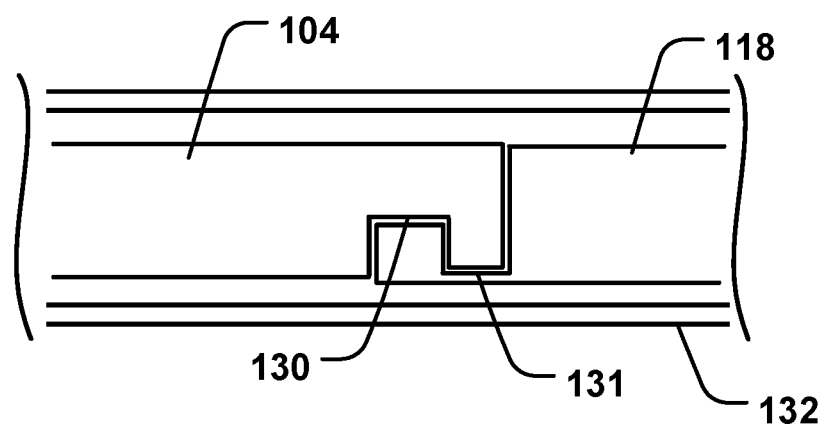
FIG. 4e is a schematic illustration, in a cross-sectional view, of a stiffening unit and a delivery unit thereof, according to an example.

FIG. 4e show one example of a delivery unit 118 configured to connect to the stiffening unit 104. In this example the delivery unit 118 and stiffening unit 104 comprises an interlocking structure 130, 131, formed as corresponding recesses 130, 131, shaped to interlock into each other. The delivery unit 118 and stiffening unit 104 may be delivered through an additional sheath 132. The sheath 132 maintains the interlocking structures 130, 131, in the locked position. When the sheath 132 is retracted, the interlocking structure 130, 131, may be released, so that the stiffening unit 104 is delivered, and the delivery unit 118 can be retracted.

Figure 8A:
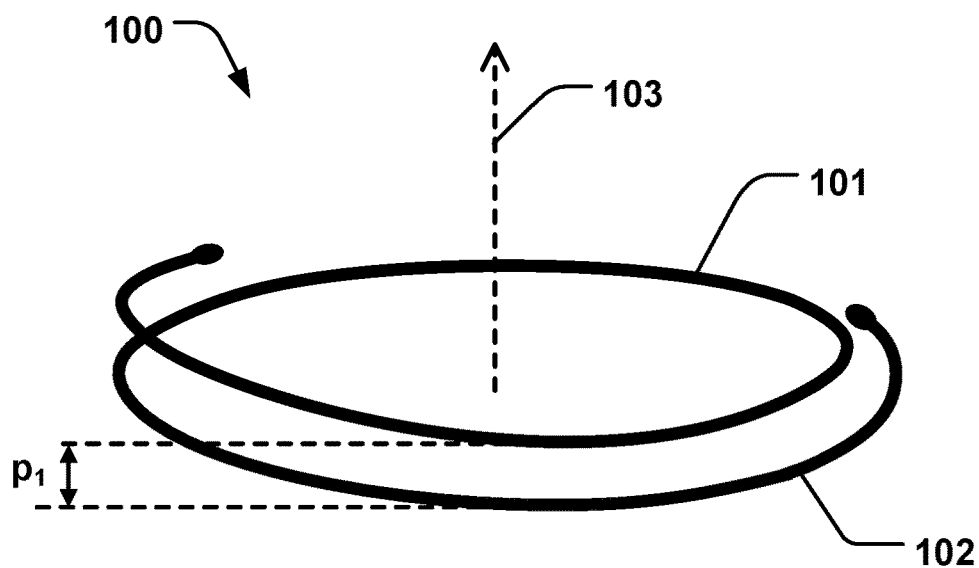
FIG. 8a is a schematic illustration of an annuloplasty device with first and second support rings separated with a first pitch distance in an axial direction, in a first configuration, according to an example.
Figure 8B:
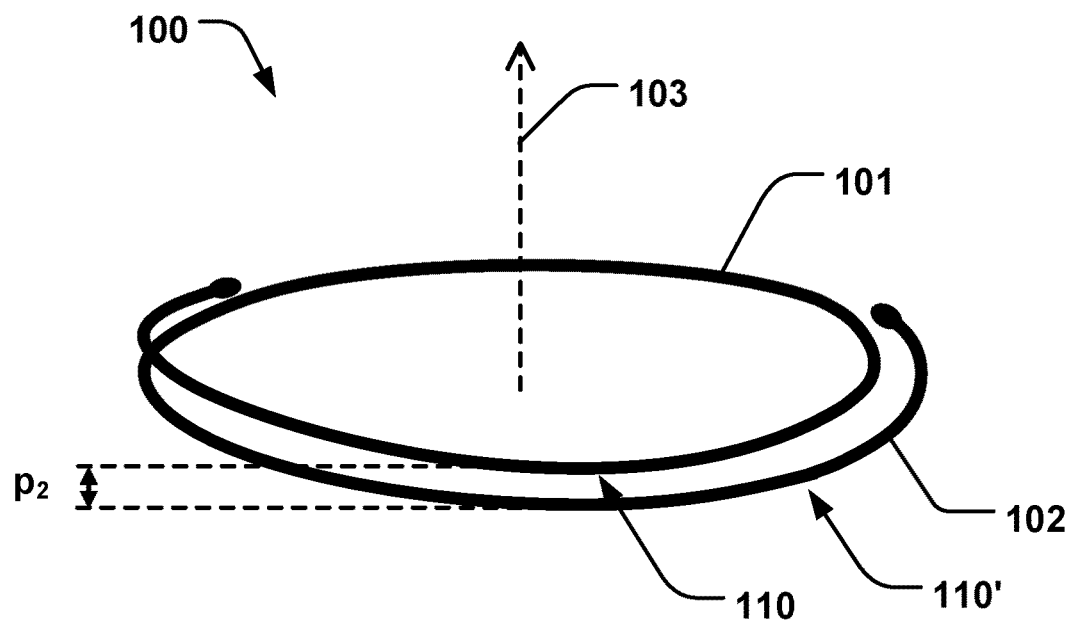
FIG. 8b is a schematic illustration of an annuloplasty device with first and second support rings separated with a second pitch distance in the axial direction, in a contracted state, according to an example.

The first and second support rings 101, 102, may be separated with a first pitch distance (p1) in the axial direction 103, in a first configuration, as illustrated in FIG. 8a. The first and second support rings 101, 102, are configured to assume a contracted state having a second pitch distance (p2) in the axial direction 103 being shorter than the first pitch distance (p1), as illustrated in FIG. 8b. The pitch distance (p1, p2) is the distance of the separation (i.e. gap) between the adjacent support rings 101, 102, in the axial direction 103. The first and second support rings 101, 102, are configured to be transferable between the first configuration and the contracted state, thereby allowing for pinching the heart valve leaflets 302 when positioned in place as illustrated in e.g. FIGS. 5a and 5d. The force by which the rings 101, 102, pinch the leaflets from the opposite sides thereof may thus be increased further, providing for a secure positioning and further enhancing cell growth in the vicinity of the support rings 101, 102.

The insertion of the stiffening unit 104 into the interior channel 105 may cause the first and second support rings to transfer from the first configuration to the contracted state. I.e., the pitch distance may be reduced from p1 to p2 as the stiffening unit 104 is inserted into the interior channel 105, which provides for an efficient and facilitated manner by which the pitch distance can be reduced. The pitch distance of adjacent coils of the stiffening unit 104 may be varied to affect the pitch distance of the adjacent first and second support rings 101, 102, along which the stiffening unit 104 extends. Hence, the stiffening unit 104 may exert a force onto the first and second support rings 101, 102, to cause them to transfer to the compressed state (as schematically indicated by the opposed directed arrows in FIG. 9a). The stiffening unit 104 thus provides for a facilitated manipulation of the pitch distance (p1, p2) between the first and second support rings 101, 102.

In one example, insertion of the stiffening unit 104 into the interior channel 105 may cause the first and second support rings 101, 102, to transfer from the first configuration to the contracted state. I.e. the stiffening unit 105 may have a relaxed heat set shape in which the distance between adjacent coils of the stiffening unit 104 may correspond to the second pitch distance (p2). The first and second support rings 101, 102, may have a relaxed heat set shape in which the distance between the adjacent first and second support rings 101, 102, may correspond to the first pitch distance (p1). The first and second support rings 101, 102, may be flexible enough (i.e. more flexible than the stiffening unit 105) so that when the stiffening unit 105 is inserted into the interior channel 105, the first and second support rings 101, 102, are forced to also assume the second pitch distance (p2), i.e. forced to the contracted state.

In one example, the stiffening unit 104 may comprise a shape-memory material. Activation of the shape-memory material may cause the first and second support rings 101, 102, to transfer from the first configuration to the contracted state. The stiffening unit 104 may thus be actively manipulated, once in place inside the interior channel 105, so that its pitch distance is varied and thereby affecting the pitch distance (p1, p2) of the first and second support rings 101, 102, as described above. The shape-memory material may be configured to be activated in response to an activation temperature. Hence, the' temperature of the stiffening unit 104 may be changed to affect the discussed shape-change thereof.

The stiffening unit 104 may have a cross-section that allows for facilitated bending in a desired direction. E.g. the force required to bend the stiffening unit 104 in a direction in which it forms a corresponding coil shape, as the first and second support rings 101, 102, may be lower than the force required to bend in a direction in which the first and second support rings 101, 102, move to pinch the valve leaflets. A greater clamping force may thus be provided in the latter direction. For example, the stiffening unit 104 may have a rectangular cross-section, where bending is facilitated in determined directions.

Figure 6A:
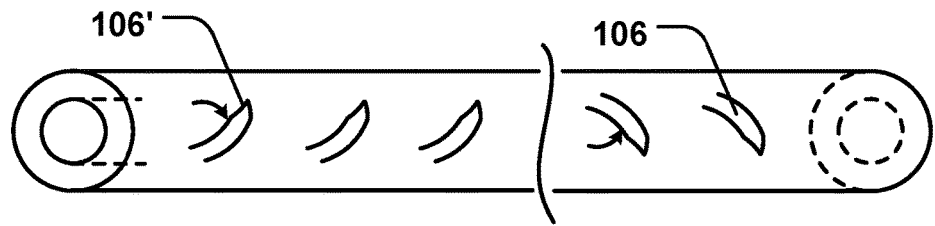
FIG. 6a is a schematic illustration of portions of the support rings of an annuloplasty device having expanded retention units, according to an example.
Figure 6B:
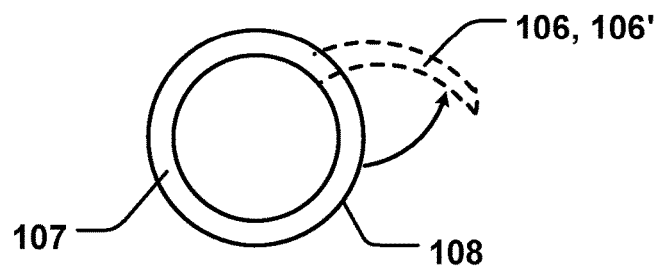
FIG. 6b is a schematic illustration, in a cross-sectional view of FIG. 6a, of a support ring of an annuloplasty device having expanded retention units, according to an example.
Figure 6C:
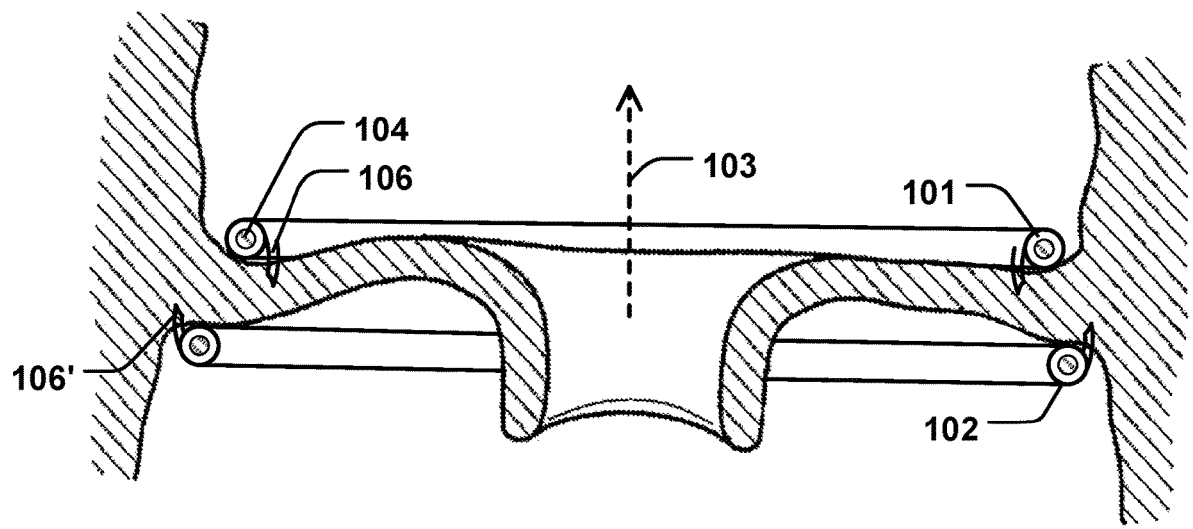
FIG. 6c is a schematic illustration of first and second support rings of an annuloplasty device arranged in a coiled configuration on opposite sides of heart valve leaflets, and expanded retention units engaged into valve tissue, according to an example.
Figure 7A:
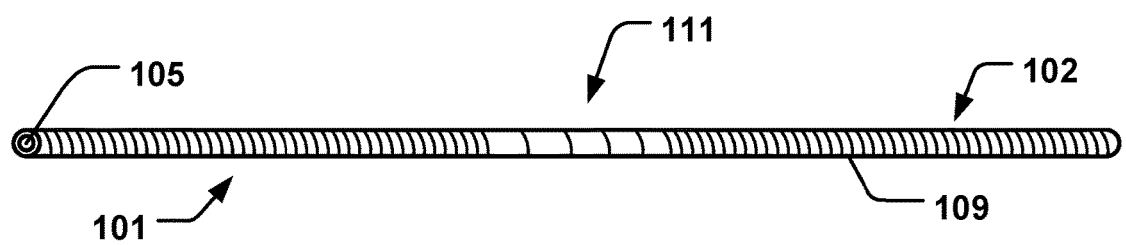
FIG. 7a is a schematic perspective view of an annuloplasty device, according to an example.
Figure 10A:
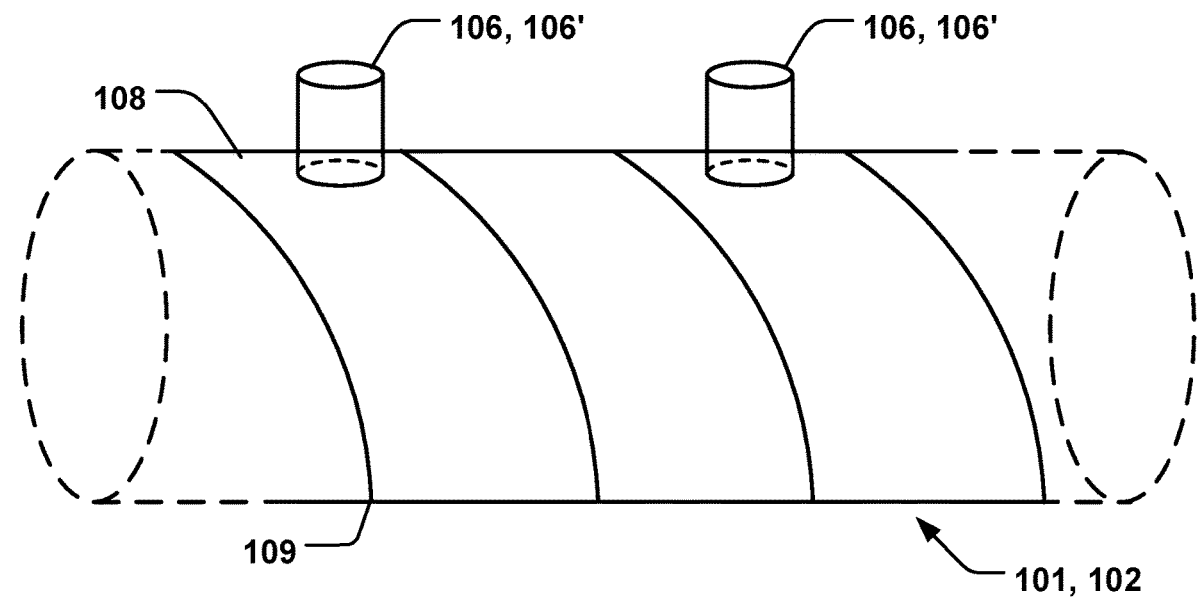
FIG. 10a is a schematic illustration, in a perspective view, of a support ring of an annuloplasty device having retention units, according to an example.
Figures 10B, 10C:
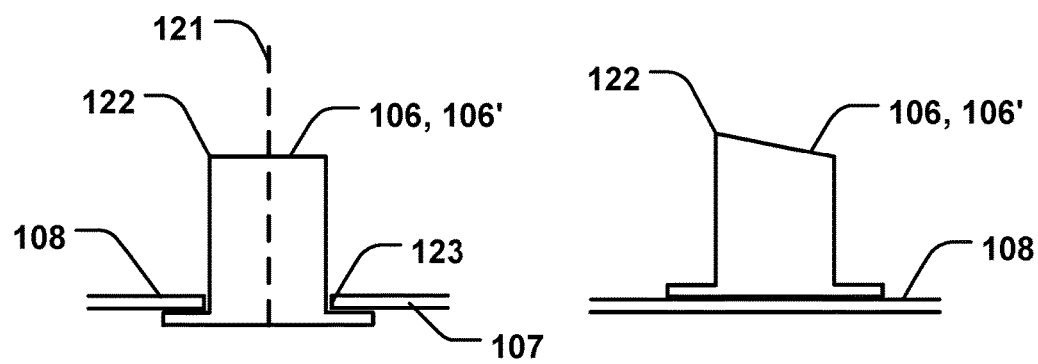
FIGS. 10b-c are schematic illustrations, in cross-sectional side views, of a support ring of an annuloplasty device having retention units, according to an example.

The annuloplasty device 100 may comprise retention units 106, 106', integrated with the first and/or second support rings 101, 102. FIG. 6a shows an example of elongate sections of the first and second support rings 101, 102, having respective retention units 106, 106'. FIGS. 10a-c show further examples of retention units 106, 106', as will be described further below. FIG. 6b show an example, in a cross-sectional view of FIG. 6a (i.e. looking along the longitudinal direction in which the first and second rings 101, 102, extend) where the retention units 106, 106', extend from the first and/or second support rings 101, 102. FIG. 6c show an example where the retention units 106, 106', engage into valve tissue from the opposite sides of the heart valve. Although FIG. 6c show retention units 106, 106', in the form illustrated in the example of FIGS. 6a-b it should be understood that the retention units 106, 106', may have other forms, such as illustrated in FIGS. 10a-c. This provides for an effective retention and fixation of the first and second rings 101, 102, in relation to the valve 301. It should be understood that in one example only the first or second support ring 101, 102, may comprise retention units 106, 106'. FIG. 7d, which will be described further below, is a further illustration showing retention units 106, 016', in a stretched elongated state of the annuloplasty device 100.

By having retention units 106, 106', integrated with the first and/or second rings 101, 102, a robust, less complex and more readily implementable fixation mechanism can be provided. As illustrated in e.g. FIG. 6a, a plurality of retention units 106, 106', may be provided on the respective first and second supports 101, 102. Each individual retention unit 106, 106' may engage or pierce into the tissue with a short distance, for a minimum amount of injury to the tissue. The sum of the retention force and friction created from all the retention units 106, 106', still provides for a strong fixation into the tissue. The scar healing will be quick since each individual retention unit 106, 106', as relatively small dimensions. This provides for a non-traumatic and still secure fixation of the annuloplasty device 100. Hence, the retention units 106, 106', provides for tissue fixation at multiple points across the annuloplasty device 100 instead of a few, e.g. 5 or 7 isolated stiches, resulting in reduced forces per fixation point, and no need for bulky stitching device or knotting device. There is further no risk of coronary artery occlusion or coronary sinus perforation. Hence, the annuloplasty device 100 provides for ease of operation, and a less time consuming procedure than stitching.

Figure 2A:
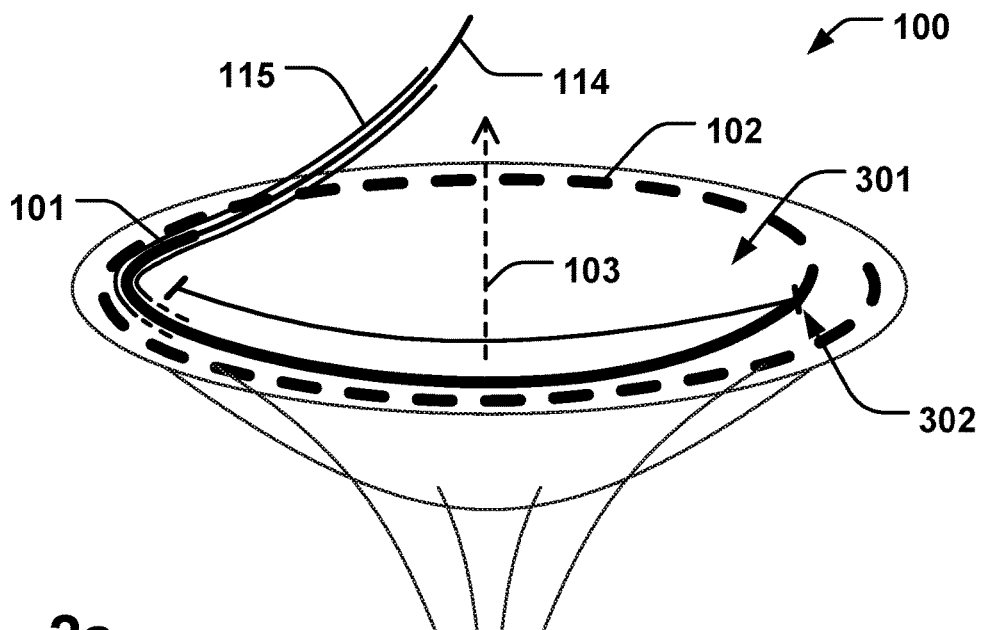
FIGS. 2a and 2c are schematic illustrations of first and second support rings of an annuloplasty device and a surrounding sheath arranged over a guide wire and in a coiled configuration on opposite sides of heart valve leaflets, according to an example.
Figure 2B:
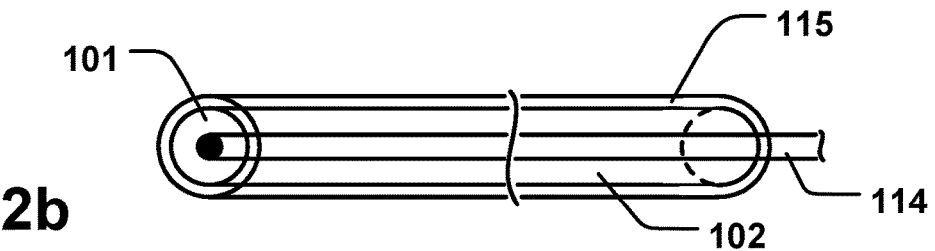
FIG. 2b is a schematic illustration, in a side-view section, of support rings of an annuloplasty device arranged inside a sheath and over a guide wire, according to an example.
Figure 2C:
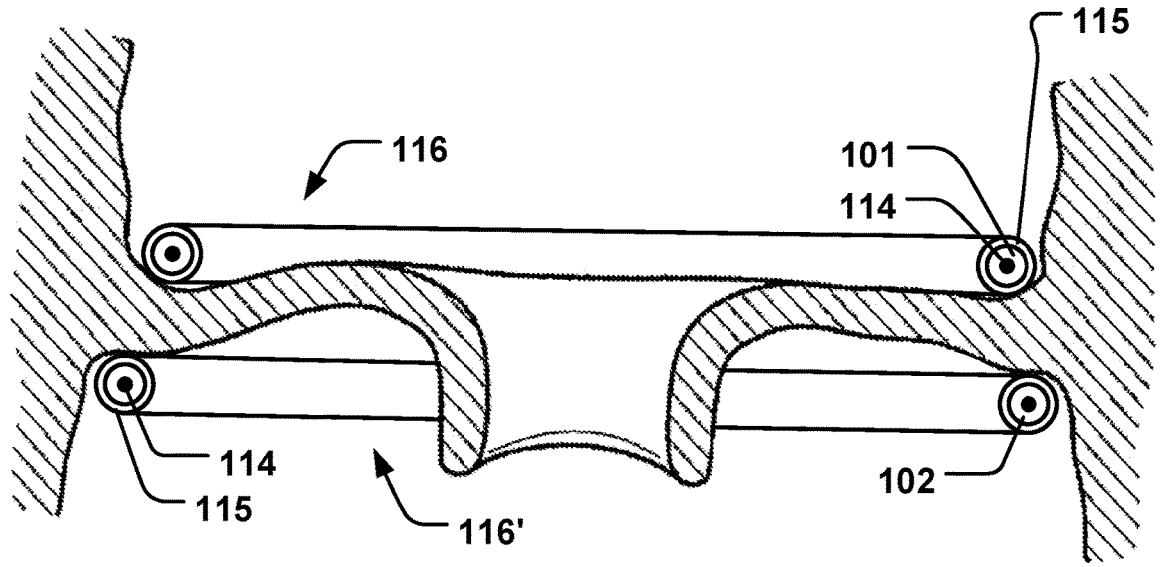
Figure 2D:
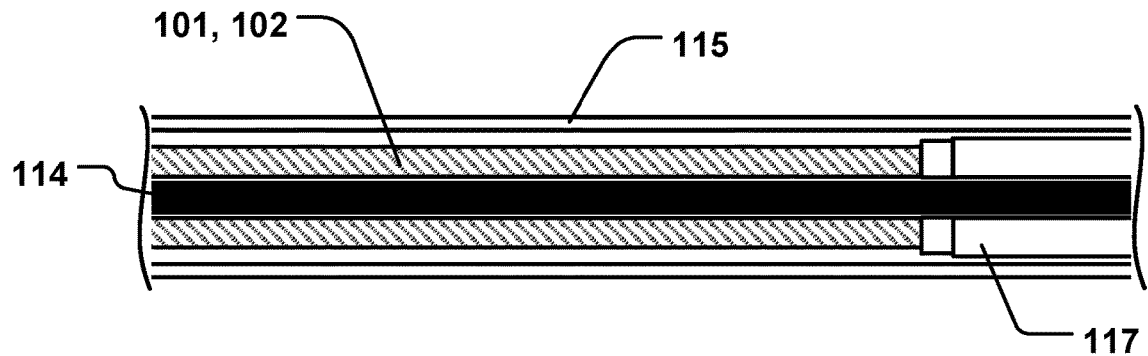
FIG. 2d is a schematic illustration, in a detailed side-view section, of a portion of a support ring of an annuloplasty device connected to a delivery device and arranged inside a sheath and over a guide wire, according to an example.
Figure 2E:
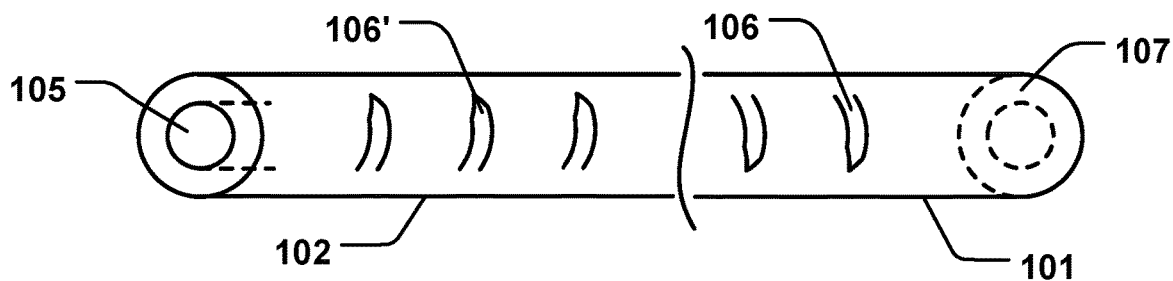
FIG. 2e is a schematic illustration of portions of the support rings of an annuloplasty device having retracted retention units, according to an example.
Figure 2F:
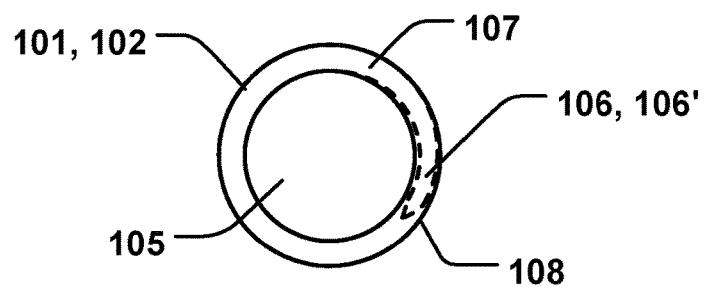
FIG. 2f is a schematic illustration, in a cross-sectional view of FIG. 2e, of a support ring of an annuloplasty device having retracted retention units, according to an example.

The first and/or second support rings 101, 102, may be formed from a material into a tubular shape with circumferential walls 107 enclosing said interior channel 105, as schematically illustrated in e.g. FIGS. 2e-f and 6b. The retention units 106, 106', may be formed from the material of the circumferential walls 107. This may provide for particularly robust and strong retention units 106. The retention units 106 may be formed from the material of the first support 101. Similarly, retention units 106' may be formed from the material of the second support 102. The retention units 106, 106', may be cut into shape from the material of the circumferential walls 107. The first and second supports 101, 102, may be integrated and formed from a continuous piece of material. Hence, the retention units 106, 106', may also be formed from such material.

The retention units 106, 106', may be cut to form various shapes for optimizing the gripping force into the tissue. The retention units 106, 106', may be formed by different cutting techniques such as milling or laser cutting techniques. It is also conceivable that the retention units 106, 106', are fixed or integrated onto the respective support rings 101, 102, by other methods, or by being formed from other materials. For example, turning to FIGS. 10a-c, the retention units 106, 106', may be separate elements rigidly attached to the first and/or second supports 101, 102. FIG. 10a is a schematic perspective view of a section of the first support 101, or the second support 102. The retention units 106, 106', may be formed as elongated pins as shown in the examples of FIGS. 10a-c. In one example, the height of the retention units 106, 106', above the surface 108 is 0.2-1 mm. A particularly advantageous height of the retention units 106, 106', above the surface 108 may be 0.3 mm. The retention units 106, 106', may thus extend in a longitudinal direction 121 and may be cut with a right angle (FIG. 10b) or an acute angle (FIG. 10c) to the longitudinal direction 121 so that a sharp edge 122 is formed which can engage surrounding tissue. The retention units 106, 106', may be arranged at a determined interval. E.g. in case the first and/or second support rings 101, 102, are formed from a spirally cut tubular material 109 the retention units 106, 106' may be attached to every, or every other (as seen in the example of FIG. 10a) loop of the spirally cut tubular material 109. The retention units 106, 106', shown in FIGS. 10a-c may be arranged as described in relation to FIG. 7d. FIG. 10b shows an example where the retention unit 106, 106', is arranged through an opening 123 in the circumferential wall 107 of the first and/or second support 101, 102. FIG. 10c show an example where the retention unit 106, 106', is attached to the surface 108 of the first and/or second support 101, 102. In both cases, the retention unit 106, 106', may be fixed by welding, by an adhesive or by other fixation elements or materials. This provides for a particularly robust and strong configuration of the retention unit 106, 106', on the annuloplasty device 100.

Turning again to the example of FIGS. 6a-b, the retention units 106, 106', may comprise a shape-memory material. Such shape memory material may be the same material from which the first and/or second supports are formed, as discussed above. Activation of the shape-memory material may cause the retention units 106, 106', to transfer from a retracted state, in which the retention units 106, 106', are flush with an outer surface 108 of the first and/or second support rings 101, 102, as illustrated in the examples of FIGS. 2e-f, to an expanded state, in which the retention units 106, 106', protrudes form the outer surface 108 of the first and/or second support rings 101, 102, as illustrated in the examples of FIGS. 6a-b. This provides for facilitated positioning of the first and second support rings 101, 102, while the retention units 106, 106', are retracted, while an efficient fixation is attained in the implanted state of the rings 101, 102, when the retention units 106, 106', are expanded.

The shape-memory material may be configured to assume the expanded state of the retention units 106, 106', in response to an activation temperature. For example, the temperature may be increased to an activation temperature, so that the retention units 106, 106', assume the expanded state. It is conceivable that the annuloplasty device 100 and the retention units 106, 106', thereof may be kept at a defined temperature while arranged in a delivery catheter. Subsequently, when the device 100 is exposed to the warm tissue, the activation temperature may be reached, so that the retention units 106, 106', can be forced into the tissue. In one example the first and second support rings 101, 102, may be formed from a shape-memory material that may cause a decrease of the pitch distance (p1, p2), as discussed above, in response to an activation temperature. A synergetic effect for fixation of the annuloplasty device 100 may thus be utilized as the rings 101, 102, contract to pinch the valve tissue and the retention units 106, 106', expand to engage into the tissue. A further emphasized effect may be provided by the stiffening unit 104 which provides for increasing the rigidity of the rings 101, 102, as discussed above, so that retention units 106, 106', can engage the tissue with an enhanced retention force. The stiffening unit 104 may in addition push the rings 101, 102, towards each other from the opposite sides, as described above, to further add to the retention force of the rings 101, 102, against the tissue. A particularly efficient and secure implantation can thus be realized.

The first and/or second support rings 101, 102, may be formed from a spirally cut tubular material 109 enclosing the interior channel 105. FIG. 7a show a schematic example of such spirally cut tube, i.e. shown as the elongated form of the first and second rings 101, 102, when stretched apart, before assuming the coiled shape. The spirally cut material provides for an enhanced flexibility of the first and second support rings 101, 102. The length of the spirally cut portions of the tube 109 may vary to adapt the flexibility along the portions of the annuloplasty device 100 and thereby tailor the device 100 to various anatomies. In the example of FIG. 7a, a portion 111 corresponding to an anterior portion 111 (see e.g. FIG. 5a) of the device 100 when in the coiled shape, has been spirally cut with a greater separation between adjacent loops of the spirally cut material compared to the cuts in the remaining length of the first and second supports 101, 102. The rigidity of the anterior portion 111 may thus be increased so that the annuloplasty device 100 is less bent along this portion or assumes a substantially straight shape. Alternatively, portion 111 is not spirally cut at all. Having a few cuts may however improve the flexibility when delivering the annuloplasty device 100 through a catheter. The annuloplasty device 100 may thus assume a D-shape in a facilitated manner. Other shapes may be provided by varying the flexibility as described.

Further, the first support ring 100 may be adapted to be arranged on an atrial side of the heart valve, and the second support ring 102 may be adapted to be arranged on a ventricular side of the heart valve, as illustrated in e.g. FIG. 5d. The first support ring 101 may comprise a first posterior bow 110 and the second support 102 may comprise a second posterior bow 110'. The first and second posterior bows 110, 110', may be adapted to conform to a posterior aspect of the heart valve, and the first and second posterior bows may be separated by the intermediate anterior portion 111. The anterior portion 111 may comprise a smooth surface, and the first and second posterior bows 110, 110', may comprise the spirally cut tubular material enclosing the interior channel 105. Having a smooth surface at the anterior portion reduces the risk of complications from damaging the tissue at this sensitive region of the valve. A smooth surface may be provided by having few or no spirally formed cuts as described above. Also, the retention units 106, 106', may be arranged on respective first and second posterior bows 110, 110', as illustrated in FIG. 7d (when the annuloplasty device 100 is in the elongated stretched state). This provides for avoiding piercing the tissue at an anterior portion 111, which can be associated with a greater risk of complications.

Hence, the first and second posterior bows 110, 110', may be separated by an intermediate anterior portion 111. First retention units 106 may be arranged with an off-set distance 113 from second retention units 106', as illustrated in FIG. 7d, so that the anterior portion 111 may comprise a smooth surface free from retention units 106, 106'. I.e. the first and second retention units 106, 106', may be arranged with an off-set distance 113 from the anterior portion 111 towards respective first and second posterior bows 110, 110'. The off-set distance 113 may be varied to optimize the annuloplasty device 100 to the particular anatomy while ensuring that there is no risk of piercing the tissue at the anterior side of the valve. The first support 101 may have the retention units 106 extending in a first direction, and the second support 102 may have the retention units 106' extending in an opposite direction.

Thus, the first support ring 101 may comprise first retention units 106, and the second support ring 102 may comprise second retention units 106'. The first and second retention units 106, 106', may extend from respective first and second retention portions 112, 112', to produce a retention force, in use, at both of said opposite sides, see FIG. 7d in conjunction with FIG. 5a. Having retention units 106, 106', at both sides of the valve provides for increasing the retention force and the strength by which the annuloplasty device 100 is fixated at the valve. The retention units 106, 106', engage the tissue from both of the mentioned sides, creating a strong retention force in the radial direction, i.e. perpendicular to the axial direction 103. The first and second supports 101, 102, pinch the tissue from both sides of the valve, so that the retention units 106, 106', a forced into the tissue. The retention units 106, 106', provides for shaping the annulus as desired even with a reduced pinching force, since the retention units 106, 106', provides for fixating the shape of the annulus in the radial direction because of the mentioned retention force. This provides for a more reliable implantation at the heart valve, both in the short term and in the long term.

The first and second retention units 106, 106', may extend in opposite directions along the axial direction 103, as illustrated in the example in e.g. FIG. 6c. I.e. the first and second retention units 106, 106', may extend from respective retention portions 112, 112', towards eachother, to clamp the tissue therebetween. It is conceivable however that the retention units 106, 106', may extend in different directions. The second retention units 106' may for example extend with an angle in a radially outward direction to engage tissue in a direction towards a tissue wall radially outside the annulus. FIG. 6c show only a few retention units 106, 106', for a more clear illustration, but it should be understood that a plurality of retention units 106, 106', may extend at a defined interval along the first and second support 101, 102, as shown in FIG. 7d and in FIG. 9b when the device 100 has a coiled configuration.

Further, the position of the first retention units 106 may be off-set in the radial direction (perpendicular to the axial direction) with respect to the second retention units 106', as schematically illustrated in FIG. 6c. Thus, although both the first and second retention units 106, 106', may extend in the vertical direction, the risk of having the first retention units 106 to engage with the second retention units 106' is avoided, which otherwise may lead to fully penetrating the valve tissue. This may be realized by having different diameters of the support rings 101, 102, and/or by arranging the first and second retention units 106, 106', to extend from opposite sides (in the radial direction of FIG. 6c) of the respective support rings 101, 102. Furthermore, when the support rings 101, 102, are arranged in the coiled configuration, the first retention units 106 may be off-set with a distance 124 with respect to the second retention units 106', as schematically illustrated in FIG. 7e. This further minimizes the risk of having two opposite retention units 106, 106', contacting each other which could accordingly result in a complete penetration of the tissue.

The first retention units 106 may be arranged along at least a first retention portion 112 of the first support ring 101, and the second retention units 106' may be arranged along at least a second retention portion 112' of the second support ring 102. The first and second retention portions 112, 112', may be curved in the coiled configuration. Hence, the retention units 106, 106', may be arranged to extend along the curved shape of the coil- or helix shaped annuloplasty device 100. The first retention portion 112 may be configured to follow the curvature of the annulus of the heart valve, such as the mitral- or tricuspid valve. The second retention portion 112' may be configured to follow the shape of the valve from the ventricular side.

The annuloplasty device 100, i.e. annuloplasty implant 100, may comprise a shape memory material, such as NiTiNol, or another suitable biocompatible alloy that can be heat-set in defined shapes, in a heat treatment procedure. The shape-memory material may comprise a material having more than one phase, so that the shape of the support rings 101, 102, and the retention units 106, 106', may be actively varied as described above. The shape memory material can be conceived as any material that is able to change shape as desired, in response to outside interaction, for example with an energy source, such as providing heat and/or electromagnetic energy, that can be transferred to the implant to change its shape. It is also conceivable that the shape of the implant can be affected by direct mechanical manipulation of the curvature of the ring-shape of the implant 100, e.g. by transferring a force or torque to the implant 100 via a delivery device. Via the various mentioned shape-affecting procedures the implant 100 may assume an elongated delivery configuration for advancement in a catheter, an initial shape when positioned in a coiled configuration along the annulus of the valve, and also an activated shape such as the contracted state described above for enhancing the strength of the fixation at an annulus of the heart valve.

Figure 7B:
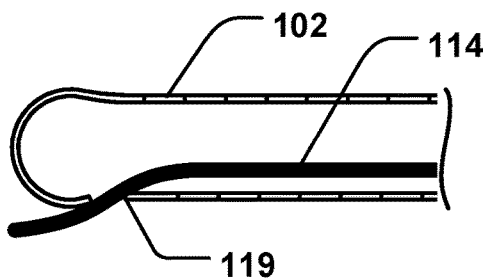
Figure 7C:
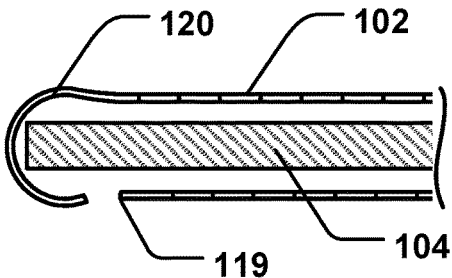
Figure 7D:
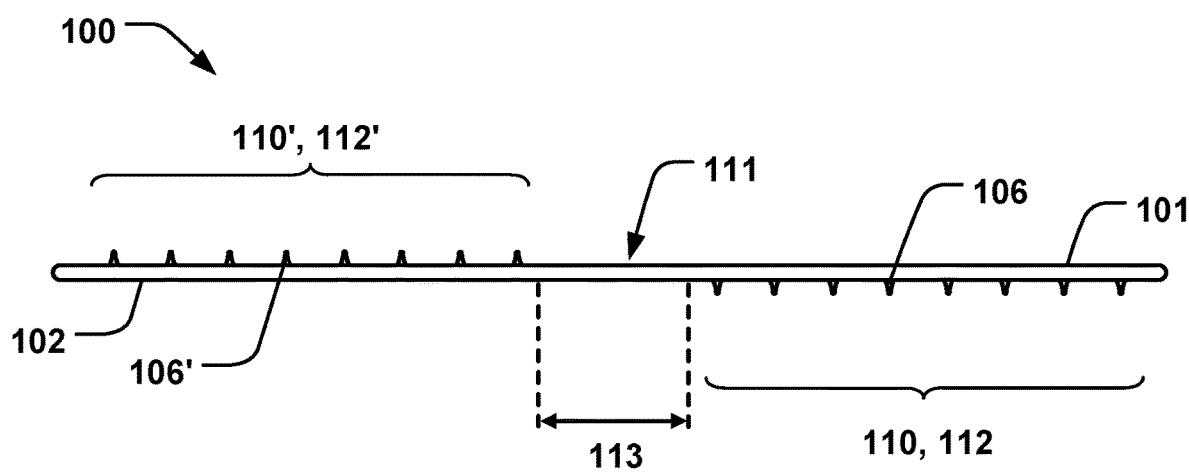
FIG. 7d is a schematic perspective view of an annuloplasty device, according to an example.

FIGS. 7b-c and 7f-i are schematic illustrations, in side view sections, of a distal portion of a support ring, such as the second support ring 102, of the annuloplasty device 100. The support ring 102 may comprise an opening 119 adjacent the distal end thereof, as exemplified in FIGS. 7b-c and 7f-i. The opening 119 may be sized so that a guide wire 114 may slide therethrough. Thus, the first and second support rings 101, 102, connected to form a tube 109, may be advanced over the guide wire 114. In this example, the guide wire 114 may pass along the interior channel 105, between opening 119 and a proximal opening (not shown) of the first support ring 101. The opening 109 adjacent the distal end of the second support ring 102 may be arranged in the side of the wall of the tube 109, as schematically illustrated in FIGS. 7b-c, or at a tip of the distal end, as schematically illustrated in FIGS. 7f-i. The distal end may be formed as an at least partly curved surface 120 which is curved to be atraumatic when pushed against the tissue. Having the opening 119 arranged through the side wall of the tube 109 allows for having the interior channel 105 of support ring 102 closed along the longitudinal direction in which the support ring 102 extends. The stiffening unit 104 may thus be inserted into the interior channel 105 until it abuts the closed distal end of the support ring 102, as schematically illustrated in FIG. 7c. Correct placement of the stiffening unit 105 may thus be facilitated after the guide wire 114 has been withdrawn. Alternatively, when having the opening 119 at the tip along the longitudinal direction of the support 102 as shown in FIGS. 7f-l, the opening 119 may have a smaller diameter than the stiffening unit 104, so that the latter can not pass through the opening 119 (FIGS. 7g and 7i). I.e. only the guide wire 114 may pass through opening 119 (FIGS. 7f and 7h). FIGS. 7h-l shown an example where a restriction element 126 at the distal end has an opening with a diameter which is less than the stiffening unit 104.

Figure 9B:
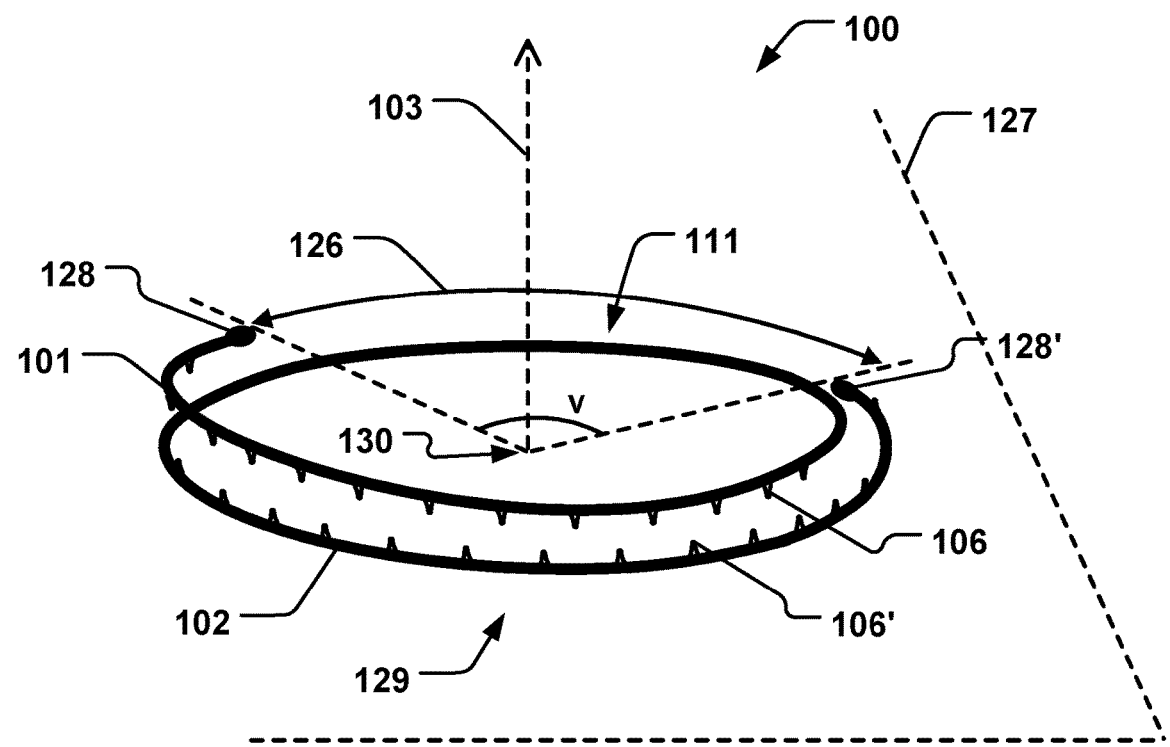
FIG. 9b is a schematic illustration, in a perspective view, of an annuloplasty device having retention units and off-set free ends, according to an example.

The first and second support rings 101, 102, may have respective free ends 128, 128', as illustrated in FIG. 9b. The free ends 128, 128', may be configured to be arranged on opposite sides of the native heart valve leaflets. The two free ends 128, 128', may be displaced from each other with a peripheral off-set distance 126 extending in a coil plane 127, as schematically illustrated in FIG. 9b. The coil plane 127 is substantially parallel to an annular periphery 129 of the coil formed by the first and second support rings 101, 102, and perpendicular to the axial direction 103. The coil plane 127 accordingly corresponds to the plane spanned by the annular periphery 129 of the device 100 when assuming the coiled configuration. The peripheral off-set distance 126 between the two free ends 128, 128', thus extends substantially perpendicular to the central axis 103. This means that, when the device 100 is positioned in the implanted state, around the annulus of the heart valve, the two free ends 128, 128', will be separated along the plane of the valve. By having such off-set 126 in the plane of the valve, the resulting reduced length of the first or second support rings 101, 102, will allow for reducing the number of retention units 106, 106', required to securely fixate the device 100 at the valve, while at the same time providing for a sufficient overlap of the first and second support rings 101, 102, on the opposites sides of the valve to attain a sufficiently strong pinching effect therebetween to fixate the annulus in a modified shape. In situations, placing retention units 106, 106', on the anterior side may be associated with high risk. This can therefore be avoided, by having the off-set 126 as specified. Further, the anterior portion 111 may not be provided by retention units 106, 106', as has described above. Furthermore, the interference of the device 100 with the movements of the valve will be minimized when having an off-set 126. Fastening of the device 100 on the atrial side can thus be accomplished by fixation of the posterior bow 110, and there will be no interference on the atrial side with the movement of the valve, due to the off-set distance 126 reducing the circle sector of the first support 101. The coil of the first and second support rings 101, 102, may have a geometrical center point 130. The angle (v) between lines extending from respective free end 128, 128', and intersecting the center point 130, as illustrated in FIG. 9b, may be approximately 90 degrees.

Figure 11A:
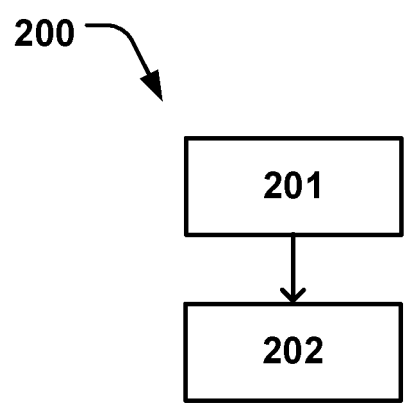
FIG. 11a is a flow chart of a method of repairing a defective heart valve according to one example.

A method 200 of repairing a defective heart valve is disclosed. The method 200 is schematically illustrated in FIG. 11a, in conjunction with FIGS. 1-6. The order in which the steps are described should not be construed as limiting, and it is conceivable that the order of the steps may be varied depending on the particular procedure. The method 200 comprises positioning 201 first and second support rings 101, 102, of an annuloplasty device 100 in a first configuration as a coil on opposite sides of native heart valve leaflets of the heart valve, as schematically illustrated in e.g. FIGS. 3a and 3d. The method 200 comprises increasing the stiffness of the first and/or second support rings 101, 102, by inserting 202 a stiffening unit 104 into an interior channel 105 arranged in at least part of the first and/or second support rings 101, 102, as schematically illustrated in FIGS. 4a-d, and FIGS. 5a-d. As discussed, the mentioned examples show the stiffening unit extending through both the first and second support rings 101, 102, length of the portion in the first and second support rings 101, 102, in which the stiffening unit 104 extends may be varied to change the rigidity of different sections of the annuloplasty device 100. Having a stiffening unit 104 arranged in the interior channel 105 provides for the advantageous benefits as discussed above in relation to the annuloplasty device 100 and FIGS. 1-10.

Figure 11B:
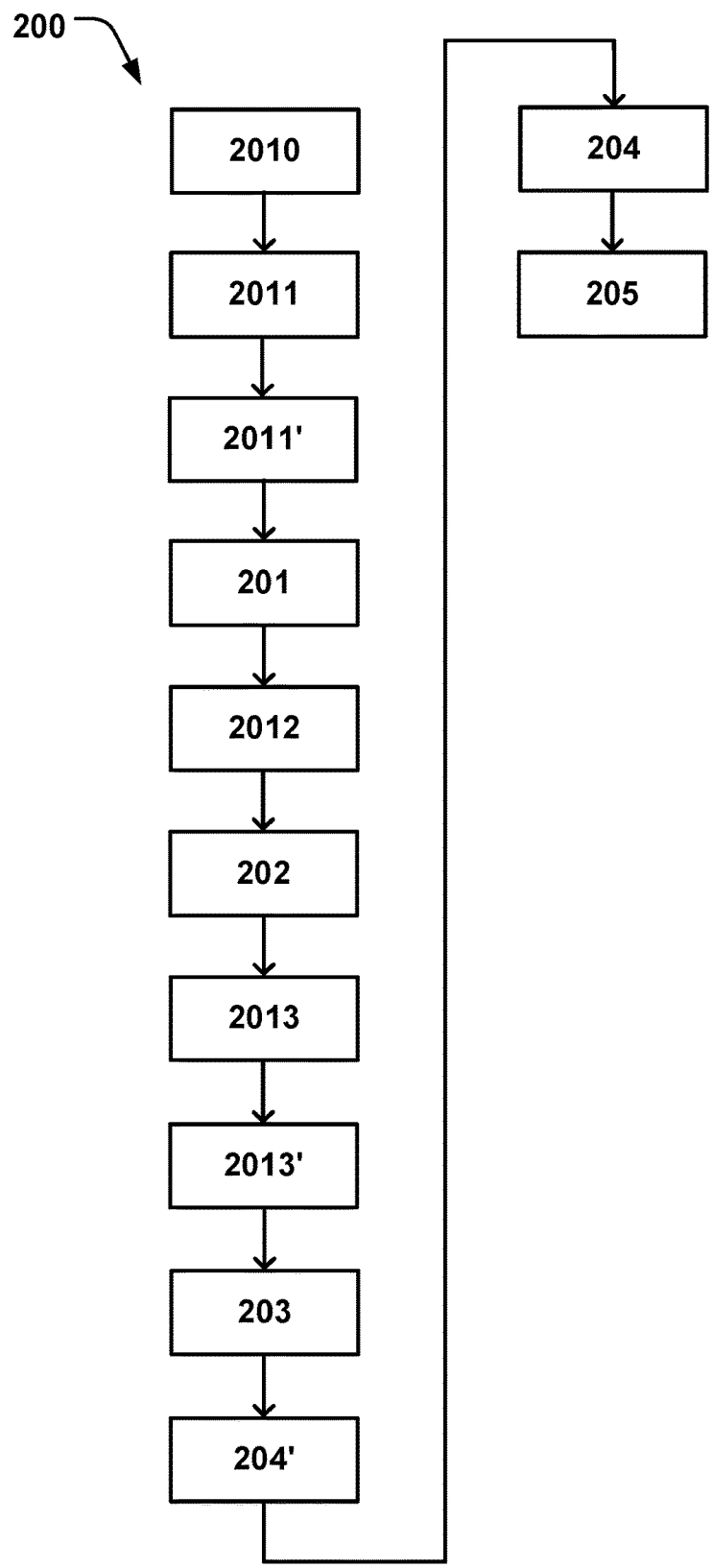
FIG. 11b is another flow chart of a method of repairing a defective heart valve according to one example.

A method 200 is schematically illustrated in FIG. 11b, in conjunction with FIGS. 1-6. The order in which the steps are described should not be construed as limiting, and it is conceivable that the order of the steps may be varied depending on the particular procedure. Positioning the first and second support rings 101, 102, may comprise advancing 2011 the first and second support rings 101, 102, over a guide wire 114 extending through the interior channel 105 to assume said coil on the opposite sides of the heart valve. FIGS. 1a and 1c show a guide wire 114 arranged as a coil at the opposite sides, extending through a valve commissure 302. The dashed line portion correspond to the portion of the guide wire 114 arranged on the ventricular side. The first and second support rings 101, 102, may thus be pushed over the guide wire 114 so that the first and second supports 101, 102, are guided into a similar coiled configuration as the guide wire 114, as illustrated in the example of FIGS. 2*a-d*. The method 200 may comprise advancing 2011' a sheath 115 and the first and second support rings 101, 102, arranged inside the sheath 115, over the guide wire 114 to assume respective coiled shapes thereof at the opposite sides of the valve, as schematically illustrated in FIGS. 2*a-d*.

The method 200 may subsequently comprise retracting 2012 the guide wire 114, as schematically illustrated in FIGS. 3*a-d*, leaving an open interior channel 105. The method 200 may comprise subsequently inserting 202 the stiffening unit 104 into the interior channel 105, as schematically illustrated in FIGS. 4*a-d*. The sheath 115 may be retracted as illustrated in FIGS. 5*a-d*, exposing the first and second rings 101, 102, in case the first and second rings 101, 102, have been inserted with a surrounding sheath 115 over the guide wire 114. The retraction of the sheath 115 may be done simultaneously as the stiffening unit 114 is inserted into the interior channel 105. The method 200 thus provides for a facilitated and secure positioning of the annuloplasty device 100 at the opposite sides of the heart valve to pinch the leaflets thereof with an increased retention force, as described above. The rings 101, 102, may be positioned with a reduced risk of entanglement in the anatomy, such as the chordae.

The method 200 may comprise activating 203 a contracted state of the annuloplasty device 100 so that a first pitch distance (p1) between the first and second support rings 101, 102, in a first configuration is reduced to a second pitch distance (p2) being shorter than the first pitch distance, as illustrated in FIGS. 8*a-b*. Thus, the first and second support rings 101, 102, move towards eachother to pinch the native heart valve leaflets. The contracted state may be activated by the insertion of the stiffening unit 104 into the interior channel 105, as described, whereby the first and second support rings 101, 102, transfer from the first configuration to the contracted state.

As elucidated above, positioning the first and second support rings 101, 102, may comprise positioning 2010 a sheath 115 to form first 116 and second 116' curves thereof as a coiled shape on the opposite sides of the native heart valve leaflets, as schematically illustrated in e.g. FIG. 2*c*. The sheath 115 may be advanced over a guidewire 114. The first and second support rings 101, 102, may then be advanced into the sheath 115, i.e. into first 116 and second 116' curves thereof. It is also conceivable that the guide wire 114 is retracted before the first and second support rings 101, 102, are advanced into position in the sheath 115. Further, it is also conceivable that two different guidewires 114 are used, having different stiffnesses. E.g. A first flexible guide wire may be used to guide the sheath 115 into the coiled configuration as explained. A second guide wire, being more rigid than the first guide wire may then be inserted into the coiled sheath 115 after the first flexible guide wire has been withdrawn. The second guidewire, having an increased stiffness, may facilitate the positioning of the first and second support rings 101, 102, which may then be advanced over the second guidewire for positioning in the sheath 115 in a coiled configuration at the opposite sides of the valve.

The method 200 may comprise ejecting 2013 the first and second support rings 101, 102, from the sheath 115 while retracting 2013' the sheath 115 such that the annuloplasty device 100 is arranged along the first and second curves 116, 116', on the opposite sides. The first and second support rings 101, 102, may thus be kept substantially stationary in relation to the heart valve when being ejected from the sheath 115 while simultaneously retracting the sheath 115. It is conceivable that the method 200 comprise positioning the first and second rings 101, 102, at the opposite sides without a guide wire 114. The sheath 115 may thus in this case define a path for the annuloplasty device 100 that allows for facilitated positioning thereof without having to push the first and second rings 101, 102, into position at the valve, which may otherwise be the case when the delivery catheter is kept stationary and the implant is ejected from the catheter. This also provides for an atraumatic positioning of the annuloplasty device 100.

As described above, retention units 106, 106', may be arranged on the first and/or second support rings 101, 102. The retention units 106, 106, may thus be engaged 204 of forced into tissue of the heart valve from the opposite sides when the sheath 115 is retracted, as illustrated in e.g. FIG. 6*c*. The sheath 115 may thus provide for protecting the tissue from the retention units 106, 106', while the rings 101, 102, are being placed into the correct position, and subsequently expose the retention units 106, 106', when gradually retracted.

The method 200 may comprise forcing 205 the retention units 106, 106', into the tissue by the insertion of the stiffening unit 104 into the interior channel 105. This provides for further increasing the retention of the annuloplasty device 100 at the heart valve as described above.

The retention units 106, 106', may comprise a shape-memory material, and the method 200 may comprise activating 204' the shape-memory material to cause the retention units 106, 106', to transfer from a retracted state (FIGS. 2*e-f*), in which the retention units 106, 106', are flush with an outer surface 108 of the first and/or second support rings 101, 102, to an expanded state (FIGS. 6*a-c*), in which the retention units 106, 106', protrudes form the outer surface 108 of the first and/or second support rings 101, 102. As described, the shape-memory material may comprise a material which is responsive to temperature, and increasing the temperature may cause the retention units 106, 106', to expand. The expansion of the retention units 106, 106', may start already when positioned inside the sheath 115 when arranged in the body.

As mentioned, the opposite sides may be an atrial side of the heart and a ventricular side of the heart. A first curve 116 of the sheath 115 may be arranged along an annulus of the heart valve on the atrial side, and a second curve 116' of the sheath 115 may be arranged around chordae of the heart valve on the ventricular side.

The present invention has been described above with reference to specific embodiments. However, other embodiments than the above described are equally possible within the scope of the invention. The different features and steps of the invention may be combined in other combinations than those described. The scope of the invention is only limited by the appended patent claims. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

The invention claimed is:

1. Method of repairing a defective heart valve, comprising
   positioning first and second support rings of an annuloplasty device in a first configuration as a coil on opposite sides of native heart valve leaflets of the heart valve, and
   increasing the stiffness of the positioned first and/or second support rings by inserting a stiffening unit into an interior channel arranged in at least part of the first and/or second support rings,
wherein positioning the first and second support rings comprises:
advancing the first and second support rings over a guide wire extending through the interior channel to assume said coil on the opposite sides;
the method subsequently comprising
retracting the guide wire, and
inserting the stiffening unit into the interior channel.

2. Method according to claim 1, comprising
activating a contracted state of the annuloplasty device so that a first pitch distance ($p_1$) between the first and second support rings in a first configuration is reduced to a second pitch distance ($p_2$) being shorter than the first pitch distance, whereby the first and second support rings move towards each other to pinch the native heart valve leaflets, wherein the contracted state is activated by the insertion of the stiffening unit into the interior channel, whereby the first and second support rings transfer from the first configuration to the contracted state.

3. Method according to claim 1, wherein positioning the first and second support rings comprises
positioning a sheath to form first and second curves thereof as a coiled shape on the opposite sides of the native heart valve leaflets,
ejecting the first and second support rings from the sheath while retracting the sheath such that the annuloplasty device is arranged along the first and second curves on the opposite sides.

4. Method according to claim 3, wherein the first and second support rings are kept stationary in relation to the heart valve when being ejected from the sheath while simultaneously retracting the sheath.

5. Method according to claim 3, whereby retention units arranged on the first and/or second support rings are engaged into tissue of the heart valve from the opposite sides when the sheath is retracted.

6. Method according to claim 5, comprising forcing the retention units into the tissue by the insertion of the stiffening unit into the interior channel.

7. Method according to claim 5, wherein the retention units comprise a shape-memory material, the method comprising
activating the shape-memory material to cause the retention units to transfer from a retracted state, in which the retention units are flush with an outer surface of the first and/or second support rings, to an expanded state, in which the retention units protrudes form the outer surface of the first and/or second support rings.

8. Method according claim 3, wherein the opposite sides are an atrial side of the heart and a ventricular side of the heart, wherein a first curve of the sheath is arranged along an annulus of the heart valve on the atrial side, and wherein a second curve of the sheath is arranged around chordae of the heart valve on the ventricular side.

9. Method according to claim 1, comprising
advancing the sheath and the first and second support rings over the guide wire to assume the coiled shapes thereof.

* * * * *